(12) United States Patent
Hamilton et al.

(10) Patent No.: US 10,441,170 B2
(45) Date of Patent: *Oct. 15, 2019

(54) SYSTEMS AND METHODS FOR MOBILE STATUS DETERMINATION AND DELIVERY

(71) Applicant: McKenzie Lynn Hamilton, Mapleton, UT (US)

(72) Inventors: Stanton Mark Hamilton, Mapleton, UT (US); McKenzie L. Hamilton, Mapleton, UT (US); Jacob D. Hamilton, Mapleton, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/800,192

(22) Filed: Nov. 1, 2017

(65) Prior Publication Data

US 2018/0064340 A1  Mar. 8, 2018

Related U.S. Application Data

(63) Continuation of application No. 15/293,183, filed on Oct. 13, 2016, now Pat. No. 9,854,974.

(51) Int. Cl.
| | | |
|---|---|---|
| A61B 5/00 | (2006.01) | |
| G06Q 10/10 | (2012.01) | |
| A61B 5/01 | (2006.01) | |
| A61B 5/021 | (2006.01) | |
| A61B 5/145 | (2006.01) | |
| A61B 5/1455 | (2006.01) | |
| A61B 5/22 | (2006.01) | |
| A61B 90/98 | (2016.01) | |
| G01G 19/44 | (2006.01) | |
| A61B 5/024 | (2006.01) | |

(52) U.S. Cl.
CPC ............. *A61B 5/002* (2013.01); *A61B 5/01* (2013.01); *A61B 5/021* (2013.01); *A61B 5/14532* (2013.01); *A61B 5/14552* (2013.01); *A61B 5/221* (2013.01); *A61B 90/98* (2016.02); *G01G 19/44* (2013.01); *G06Q 10/1095* (2013.01); *A61B 5/024* (2013.01); *A61B 5/14542* (2013.01); *A61B 5/14551* (2013.01); *A61B 5/222* (2013.01); *A61B 5/6895* (2013.01); *A61B 5/746* (2013.01); *A61B 2503/10* (2013.01); *A61B 2560/0209* (2013.01)

(58) Field of Classification Search
CPC ....... A61B 5/68; A61B 5/0015; A61B 5/0024; A61B 5/6801; A61B 2560/0209; A61B 2560/0214
See application file for complete search history.

(56) References Cited

U.S. PATENT DOCUMENTS

2012/0016258 A1* 1/2012 Webster ............... A61B 5/01
  600/549
2016/0321480 A1* 11/2016 Hamlin ................. G16H 10/40

* cited by examiner

*Primary Examiner* — Kevin Kim

(57) ABSTRACT

Embodiments are related to systems and methods for data determining information about a subject, and more particularly to systems and methods for utilizing and distributing information related to measurements of a human subject.

21 Claims, 10 Drawing Sheets

SYSTEMS AND METHODS FOR MOBILE STATUS DETERMINATION AND DELIVERY

RELATED APPLICATIONS

This application is a continuation of an application entitled, "Systems and Methods for Mobile Status Determination and Delivery", invented by McKenzie L. Hamilton et al., U.S. patent application Ser. No. 15/293,183, filed Oct. 13, 2016. The entirety of the aforementioned application is incorporated herein for all purposes.

FIELD OF THE INVENTION

Embodiments are related to systems and methods for data determining information about a subject, and more particularly to systems and methods for utilizing and distributing information related to measurements of a human subject.

BACKGROUND

Healthcare it traditionally delivered through a process whereby a patient makes an appointment with a provider, and while at the provider various patient statistics are gathered and used by a provider in directing the patient's care. This process is expensive and often results in misdiagnosis due to incomplete data.

Hence, for at least the aforementioned reasons, there exists a need in the art for advanced systems and methods for delivering healthcare.

SUMMARY

Embodiments are related to systems and methods for data determining information about a subject, and more particularly to systems and methods for utilizing and distributing information related to measurements of a human subject.

This summary provides only a general outline of some embodiments of the invention. The phrases "in one embodiment," "according to one embodiment," "in various embodiments", "in one or more embodiments", "in particular embodiments" and the like generally mean the particular feature, structure, or characteristic following the phrase is included in at least one embodiment of the present invention, and may be included in more than one embodiment of the present invention. Importantly, such phrases do not necessarily refer to the same embodiment. Many other embodiments of the invention will become more fully apparent from the following detailed description, the appended claims and the accompanying drawings.

BRIEF DESCRIPTION OF THE FIGURES

A further understanding of the various embodiments of the present invention may be realized by reference to the figures which are described in remaining portions of the specification. In the figures, like reference numerals are used throughout several figures to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF SOME EMBODIMENTS

Embodiments are related to systems and methods for data determining information about a subject, and more particularly to systems and methods for utilizing and distributing information related to measurements of a human subject.

Some embodiments of the present inventions provide health care delivery systems that include: a central processing server, a sensor device, and a mobile transponder. The central processing server is operable to: program a mobile transponder to be associated with an individual; and upload individual measurement data derived from a data set stored in a memory of a transponder. The sensor device is operable to: generate a measurement value corresponding to the individual; generate a radio frequency signal at a defined frequency; and transmit a message including the measurement value. The mobile transponder is wearable by the individual and includes the memory of the mobile transponder. The mobile transponder is operable to: generate power from the radio frequency signal; receive the message; and store the data set to the memory, where the data set is derived from the message including the measurement value.

Figure 1:
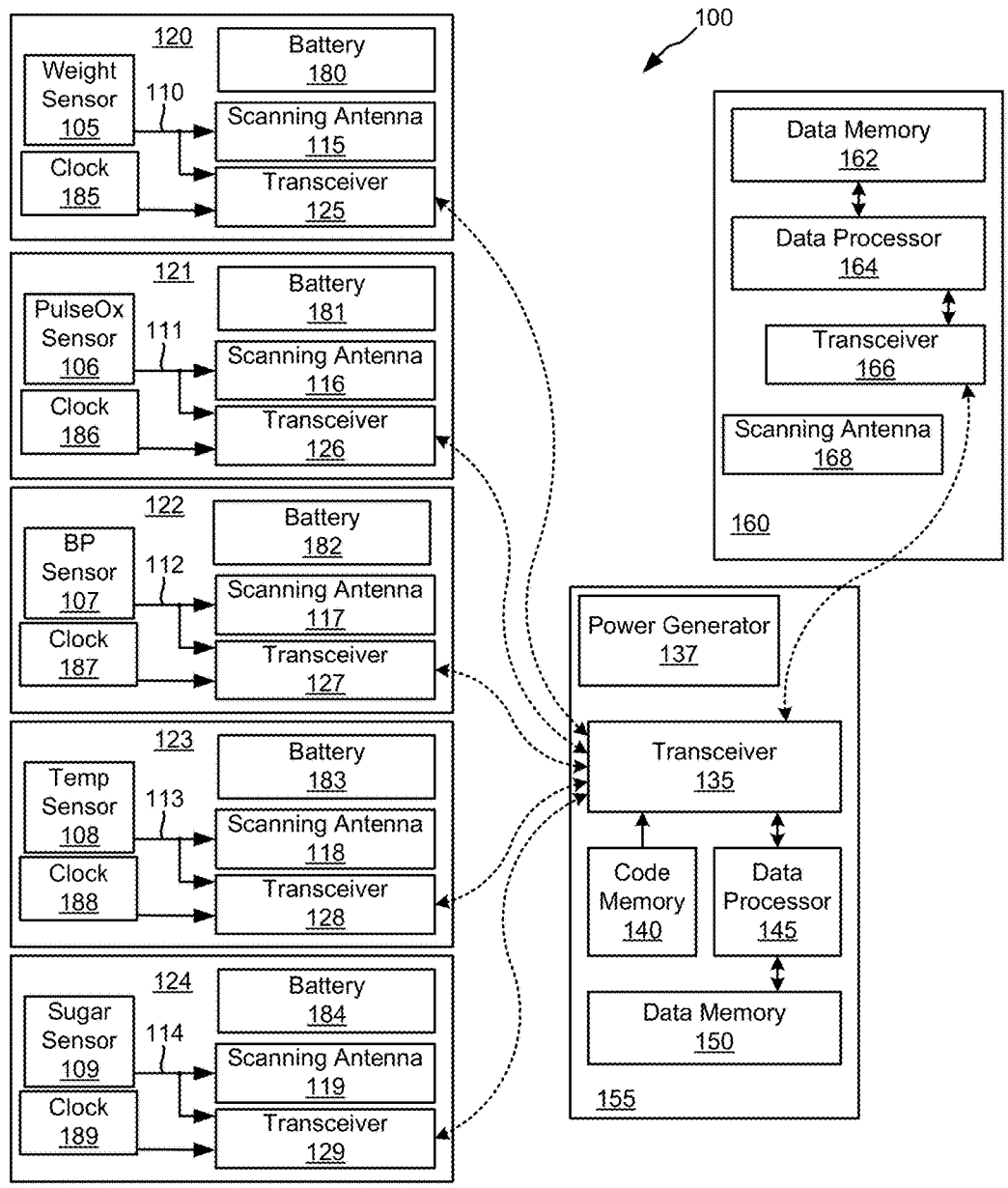
FIG. 1 shows a system including a mobile transponder powered using energy derived from a scanning antenna of one or more sensor devices in accordance with various embodiments of the present inventions.

Turning to FIG. 1, a system 100 including a mobile transponder 155 powered using energy derived from a scanning antenna 115, 116, 117, 118, 119 of one or more sensor devices 120, 121, 122, 123, 124 in accordance with various embodiments of the present inventions. System 100 also includes a host device 160 for offloading and processing data from mobile transponder 155.

Mobile transponder 155 includes a power generator 137 operable to generate power to operate mobile transponder 155 from a radio frequency signal (i.e., electromagnetic waves) generated by one or more of scanning antennas 115, 116, 117, 118, 119. The radio frequency signal may be, for example, a short range signal similar to that found in RFID systems. In some embodiments, the radio frequency signal is approximately 125 KHz. In other embodiments, the radio frequency signal is approximately 13.56 MHz. In yet other embodiments, the radio frequency signal is approximately 850-900 MHz. In yet further embodiments, the radio frequency signal is approximately 2.45 GHz. Power generator 137 includes an antenna tuned to the frequency of the radio frequency signal. When the radio frequency signal is detected by power generator 137, mobile transponder 155 is put into a powered or wake mode and the radio frequency signal is converted into power useable to operate the functions of mobile transponder 155.

Mobile transponder 155 further includes a transceiver circuit 135 that immediately transmits an identification code maintained in a code memory 140. After transmitting the identification code, transceiver circuit 135 waits a timeout period for a response from one of a number of sensor devices 120, 121, 122, 123, 124. Where no response is received, transceiver 135 times out and mobile transponder 155 is returned to a sleep mode. Alternatively, where a response is received, transceiver 135 provides the received response to a data processor 145 where it is parsed and processed. This parsing and processing may include, but is not limited to, determining the type of sensor device that provided the response, filtering the received sensor data, and where appropriate, storing the received sensor data and a corresponding timestamp to a data memory 150. In some cases, data memory 150 is a flash memory. As one example, a response may include the fields set forth below in relation to Table 1.

TABLE 1

| RQUST | Sensor Type | Sensor Data | Time |
| --- | --- | --- | --- |

The RQUST field is a single bit field set equal to a logic '1' indicating that the response is from a sensor device. Where the RQUST field is set equal to a logic '0' it indicates that the response is requesting to read data from mobile transponder 155, and the other fields (i.e., sensor type field, sensor data field, and time field) have authentication information as more fully discussed below. The sensor type field may be a ten bit field indicating a particular sensor type (e.g., weight, pulse/oxygen, blood pressure, temperature, blood sugar). As another example, the sensor type may be a particular type of exercise machine. Based upon the disclosure provided herein, one of ordinary skill in the art will recognize a variety of sensor types that may be used in relation to different embodiments. The sensor data field may be a sixty-four bit field indicating the measurement data. Thus, for example, where the sensor type is a weight sensor the sensor data may be the measured weight. As another example, where the sensor type is a treadmill the sensor data may be an exercise time, distance, and approximate calorie count. The time field is a thirty-two bit field indicating the time the measurement data was received. In some embodiments, the time may indicate an hour of the day and a date. The received sensor data may be stored in any format in data memory 150 that allows it to be retrieved at a later date.

Weight sensor device 120 includes: a weight sensor circuit 105 that operates to indicate the weight of an object placed on weight sensor device 120, a battery 180 that powers weight sensor device 120, a clock 185 that operates to indicate a time data, a scanning antenna 115 that generates a radio frequency signal, and a transceiver 125 operable to both receive an identification code from mobile transponder 155 and to transmit weight data 110 and a timestamp based upon the time data from clock 185. In operation, a subject to be measured (not shown) steps on weight sensor device 120. In response, weight sensor circuit 105 generates weight data 110 indicating the weight of the subject. Where weight data 110 exceeds a threshold value (e.g., five pounds), scanning antenna 115 and transceiver 125 are placed in a wake mode. In the wake mode, scanning antenna 115 transmits a radio frequency signal (i.e., electromagnetic waves) that may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

Transceiver 125 listens for a transmission of an identification signal from mobile transponder device 155. The identification signal is a radio frequency signal carrying the identification code accessed from code memory 140. Transceiver 125 waits a timeout period for the identification code from mobile transponder 155. Where no identification code is received, transceiver 125 times out and scanning antenna 115 and transceiver 125 are returned to a sleep mode. Alternatively, where an identification code is received, transceiver 125 transmits the weight data 110 and the timestamp based upon the time data from clock 185 to mobile transponder 155 as a response. Once the response is transmitted, scanning antenna 115 and transceiver 125 are returned to the sleep mode.

Pulse/oxygen sensor device 121 includes: a pulse and oxygen sensor circuit 106 that operates to indicate a pulse and a blood oxygen level of the subject using pulse/oxygen sensor device 121, a battery 181 that powers pulse/oxygen sensor device 121, a clock 186 that operates to indicate a time data, a scanning antenna 116 that generates a radio frequency signal, and a transceiver 126 operable to both receive an identification code from mobile transponder 155 and to transmit pulse and oxygen data 111 and a timestamp based upon the time data from clock 186. In operation, a subject to be measured (not shown) deploys pulse/oxygen sensor device 121. In response, pulse/oxygen sensor circuit 106 generates pulse and oxygen data 111 indicating a pulse and a blood oxygen level of the subject using pulse/oxygen sensor device 121. Where pulse and oxygen data 111 exceeds a threshold value (e.g., pulse greater than 30 beats per minute), scanning antenna 116 and transceiver 126 are placed in a wake mode. In the wake mode, scanning antenna 116 transmits a radio frequency signal (i.e., electromagnetic waves) that may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

Transceiver 126 listens for a transmission of an identification signal from mobile transponder device 155. The identification signal is a radio frequency signal carrying the identification code accessed from code memory 140. Transceiver 126 waits a timeout period for the identification code from mobile transponder 155. Where no identification code is received, transceiver 126 times out and scanning antenna 116 and transceiver 126 are returned to a sleep mode. Alternatively, where an identification code is received, transceiver 126 transmits the pulse and oxygen data 111 and the timestamp based upon the time data from clock 186 to mobile transponder 155 as a response. Once the response is transmitted, scanning antenna 116 and transceiver 126 are returned to the sleep mode.

Blood pressure sensor device 122 includes: a blood pressure sensor circuit 107 that operates to indicate a blood pressure of the subject using blood pressure sensor device 122, a battery 182 that powers blood pressure sensor device 122, a clock 187 that operates to indicate a time data, a scanning antenna 117 that generates a radio frequency signal, and a transceiver 127 operable to both receive an identification code from mobile transponder 155 and to transmit systolic and diastolic blood pressure data 112 and a timestamp based upon the time data from clock 187. In operation, a subject to be measured (not shown) deploys blood pressure sensor device 122. In response, blood pressure sensor circuit 107 generates systolic and diastolic blood pressure data 112 indicating a pulse and a blood oxygen level of the subject using blood pressure sensor device 122. Where systolic and diastolic blood pressure data 112 exceeds a threshold value (e.g., systolic blood pressure greater than 20 mmHg), scanning antenna 117 and transceiver 127 are placed in a wake mode. In the wake mode, scanning antenna 117 transmits a radio frequency signal (i.e., electromagnetic waves) that may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

Transceiver 127 listens for a transmission of an identification signal from mobile transponder device 155. The identification signal is a radio frequency signal carrying the identification code accessed from code memory 140. Transceiver 127 waits a timeout period for the identification code from mobile transponder 155. Where no identification code is received, transceiver 127 times out and scanning antenna 117 and transceiver 127 are returned to a sleep mode. Alternatively, where an identification code is received, transceiver 127 transmits the systolic and diastolic blood pressure data 112 and the timestamp based upon the time data from clock 187 to mobile transponder 155 as a response. Once the response is transmitted, scanning antenna 117 and transceiver 127 are returned to the sleep mode.

Temperature sensor device 123 includes: a temperature sensor circuit 108 that operates to indicate a temperature of the subject using temperature sensor device 123, a battery 183 that powers temperature sensor device 123, a clock 188 that operates to indicate a time data, a scanning antenna 118 that generates a radio frequency signal, and a transceiver 128 operable to both receive an identification code from mobile transponder 155 and to transmit temperature data 113 and a timestamp based upon the time data from clock 188. In operation, a subject to be measured (not shown) deploys temperature sensor device 123. In response, temperature sensor circuit 108 generates temperature data 113 indicating a temperature of the subject using temperature sensor device 123. Where temperature data 113 exceeds a threshold value (e.g., temperature greater than 86 degrees F.), scanning antenna 118 and transceiver 128 are placed in a wake mode. In the wake mode, scanning antenna 118 transmits a radio frequency signal (i.e., electromagnetic waves) that may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

Transceiver 128 listens for a transmission of an identification signal from mobile transponder device 155. The identification signal is a radio frequency signal carrying the identification code accessed from code memory 140. Transceiver 128 waits a timeout period for the identification code from mobile transponder 155. Where no identification code is received, transceiver 128 times out and scanning antenna 118 and transceiver 128 are returned to a sleep mode. Alternatively, where an identification code is received, transceiver 128 transmits the temperature data 113 and the timestamp based upon the time data from clock 188 to mobile transponder 155 as a response. Once the response is transmitted, scanning antenna 118 and transceiver 128 are returned to the sleep mode.

Sugar sensor device 124 (e.g., a glucometer) includes: a sugar sensor circuit 108 that operates to indicate a blood sugar level of the subject using sugar sensor device 124, a battery 184 that powers sugar sensor device 124, a clock 189 that operates to indicate a time data, a scanning antenna 119 that generates a radio frequency signal, and a transceiver 129 operable to both receive an identification code from mobile transponder 155 and to transmit sugar data 114 and a timestamp based upon the time data from clock 189. In operation, a subject to be measured (not shown) deploys sugar sensor device 124. In response, sugar sensor circuit 109 generates sugar data 114 indicating a blood sugar level of the subject using sugar sensor device 124. Where sugar data 114 exceeds a threshold value (e.g., sugar greater than 100 mg/dL), scanning antenna 119 and transceiver 129 are placed in a wake mode. In the wake mode, scanning antenna 119 transmits a radio frequency signal (i.e., electromagnetic waves) that may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

Transceiver 129 listens for a transmission of an identification signal from mobile transponder device 155. The identification signal is a radio frequency signal carrying the identification code accessed from code memory 140. Transceiver 129 waits a timeout period for the identification code from mobile transponder 155. Where no identification code is received, transceiver 129 times out and scanning antenna 119 and transceiver 129 are returned to a sleep mode.

Alternatively, where an identification code is received, transceiver 129 transmits the sugar data 114 and the timestamp based upon the time data from clock 189 to mobile transponder 155 as a response. Once the response is transmitted, scanning antenna 119 and transceiver 129 are returned to the sleep mode.

A host device 160 includes a scanning antenna 168, a transceiver 166, a data processor 164, and a data memory 162. Scanning antenna 168 transmits a radio frequency signal (i.e., electromagnetic waves) that may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

Transceiver 166 listens for a transmission of an identification signal from mobile transponder device 155. The identification signal is a radio frequency signal carrying the identification code accessed from code memory 140. Transceiver 166 waits a timeout period for the identification code from mobile transponder 155. Where no identification code is received, transceiver 166 times out. Alternatively, where an identification code is received, transceiver 166 transmits a read request to transponder 155. As one example, a read request may include the fields set forth below in relation to Table 2.

TABLE 2

| RQUST | Requestor ID | Requestor Access Code |
|---|---|---|

The RQUST field is a single bit field set equal to a logic '0' indicates that the response is requesting to read data from mobile transponder 155. Where the RQUST field is set equal to a logic '1' it indicates that the response is from a sensor device, and the other fields (i.e., requestor ID field and Requestor Access Code Field) have sensor device data as more fully discussed above in relation to table 1. In response, transponder 155 authenticates the request based upon the requestor ID field and the requestor access code field and where appropriate uploads all measure data and corresponding timestamps maintained in data memory 150 to host device 160. The received uploaded data is provided to a data processor 164 that both processes the received data and stores the received data to a data memory 162.

Figure 2:
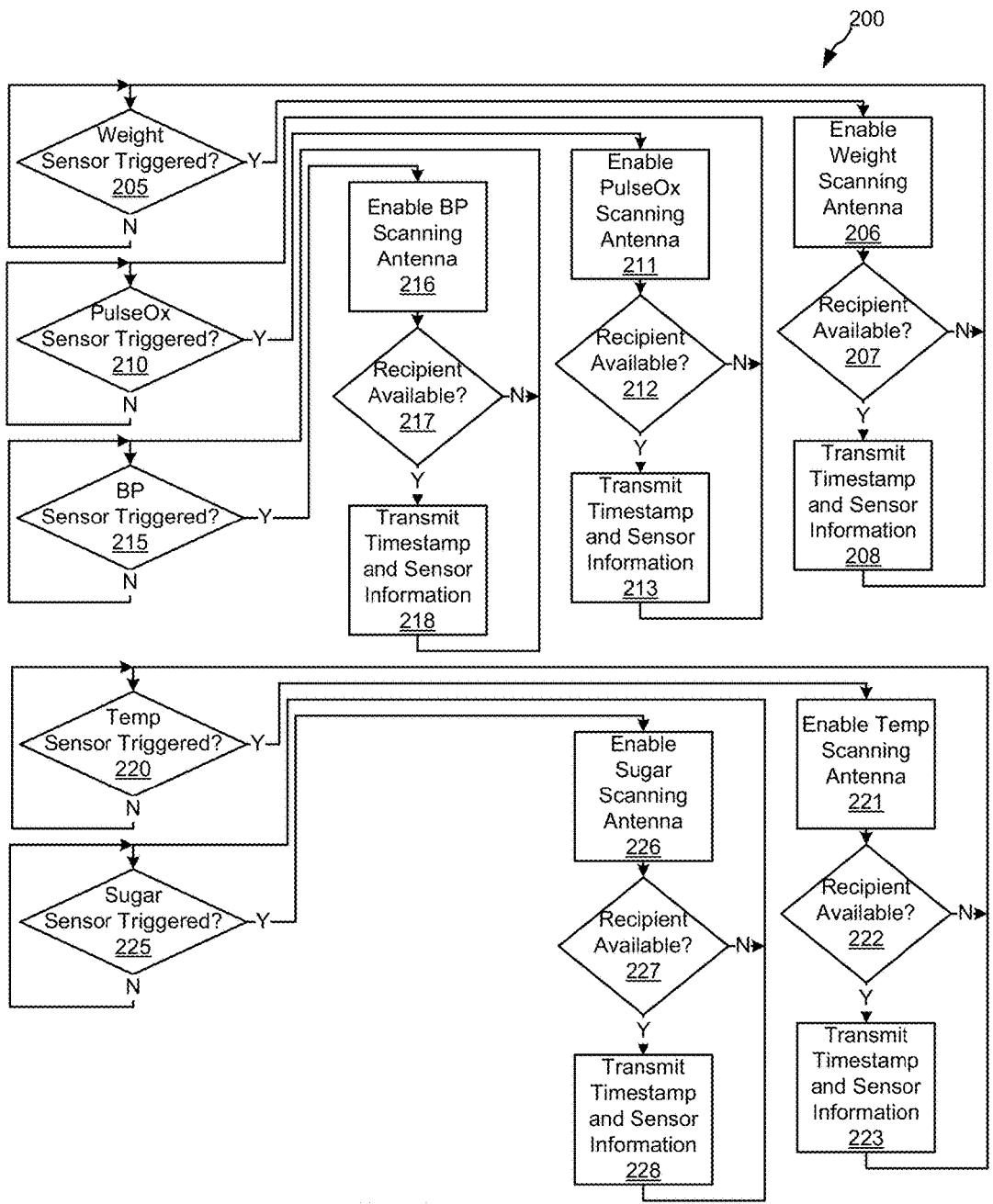
FIG. 2 is a flow diagram showing a method in accordance with one or more embodiments of the present inventions for providing patient information from various sensors to a mobile transponder.

Turning to FIG. 2, a flow diagram 200 shows a method in accordance with one or more embodiments of the present inventions for providing patient information from various sensors to a mobile transponder. Following flow diagram 200, it is determined whether a weight sensor is triggered (block 205). In some cases, the weight sensor may be considered triggered when, for example, it registers more than twenty pounds indicating that someone is using a weighing device in which the weight sensor is deployed. Where the weight sensor is triggered (block 205), a scanning antenna associated with the weighing device is enabled and begins transmitting a radio frequency signal (i.e., electromagnetic waves) (block 206). This radio frequency signal may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

The weighing device determines if a recipient of the transmission exists (block 207). This determination may be made by querying whether the weighing device receives identification information transmitted from a transponder. Where no identification is received within a timeout period (block 207), the scanning antenna is disabled or powered down to save energy. Alternatively, where identification information is received indicating a transponder is available to receive information generated by the weight sensor (block 207), the weighing device transmits a timestamp and weight data from the weight sensor (block 208). Once the transmission is complete, functionality of the weighing device is disabled to conserve power.

In parallel, it is determined whether a pulse/oxygen sensor is triggered (block 210). In some cases, the pulse/oxygen sensor may be considered triggered when it registers a pulse greater than twenty beats per minute indicating that someone is using a pulse/oxygen device in which the pulse/oxygen sensor is deployed. Where the pulse/oxygen sensor is triggered (block 210), a scanning antenna associated with the pulse/oxygen device is enabled and begins transmitting a radio frequency signal (i.e., electromagnetic waves) (block 211). This radio frequency signal may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

The pulse/oxygen device determines if a recipient of the transmission exists (block 212). This determination may be made by querying whether the pulse/oxygen device receives identification information transmitted from a transponder. Where no identification is received within a timeout period (block 212), the scanning antenna is disabled or powered down to save energy. Alternatively, where identification information is received indicating a transponder is available to receive information generated by the pulse/oxygen sensor (block 212), the pulse/oxygen device transmits a timestamp along with pulse and oxygen level data from the pulse/oxygen sensor (block 213). Once the transmission is complete, functionality of the pulse/oxygen device is disabled to conserve power.

In parallel, it is determined whether a blood pressure sensor is triggered (block 215). In some cases, the blood pressure sensor may be considered triggered when it registers a systolic blood pressure greater than twenty mmHg indicating that someone is using a blood pressure device in which the blood pressure sensor is deployed. Where the blood pressure sensor is triggered (block 215), a scanning antenna associated with the blood pressure device is enabled and begins transmitting a radio frequency signal (i.e., electromagnetic waves) (block 216). This radio frequency signal may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

The blood pressure device determines if a recipient of the transmission exists (block 217). This determination may be made by querying whether the blood pressure device receives identification information transmitted from a transponder. Where no identification is received within a timeout period (block 217), the scanning antenna is disabled or powered down to save energy. Alternatively, where identification information is received indicating a transponder is available to receive information generated by the blood pressure sensor (block 217), the blood pressure device transmits a timestamp along with systolic and diastolic blood pressure data from the blood pressure sensor (block 218). Once the transmission is complete, functionality of the blood pressure device is disabled to conserve power.

In parallel, it is determined whether a temperature sensor is triggered (block 220). In some cases, the temperature sensor may be considered triggered when it registers a temperature greater than eighty five degrees Fahrenheit indicating that someone is using a temperature device in which the temperature sensor is deployed. Where the temperature sensor is triggered (block 220), a scanning antenna associated with the temperature device is enabled and begins transmitting a radio frequency signal (i.e., electromagnetic waves) (block 221). This radio frequency signal may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

The temperature device determines if a recipient of the transmission exists (block 222). This determination may be made by querying whether the temperature device receives identification information transmitted from a transponder. Where no identification is received within a timeout period (block 222), the scanning antenna is disabled or powered down to save energy. Alternatively, where identification information is received indicating a transponder is available to receive information generated by the temperature sensor (block 222), the temperature device transmits a timestamp along with temperature data from the temperature sensor (block 223). Once the transmission is complete, functionality of the temperature device is disabled to conserve power.

In parallel, it is determined whether a sugar sensor is triggered (block 225). In some cases, the sugar sensor may be considered triggered when it registers a blood sugar level greater than one hundred mg/dL indicating that someone is using a sugar device in which the sugar sensor is deployed. Where the sugar sensor is triggered (block 225), a scanning antenna associated with the sugar device is enabled and begins transmitting a radio frequency signal (i.e., electromagnetic waves) (block 226). This radio frequency signal may be, for example, a short range signal similar to that found in RFID systems. In some embodiments, the transmitted radio frequency signal is approximately 125 KHz. In other embodiments, the transmitted radio frequency signal is approximately 13.56 MHz. In yet other embodiments, the transmitted radio frequency signal is approximately 850-900 MHz. In yet further embodiments, the transmitted radio frequency signal is approximately 2.45 GHz.

The sugar device determines if a recipient of the transmission exists (block 227). This determination may be made by querying whether the sugar device receives identification information transmitted from a transponder. Where no identification is received within a timeout period (block 227), the scanning antenna is disabled or powered down to save energy. Alternatively, where identification information is received indicating a transponder is available to receive information generated by the sugar sensor (block 227), the sugar device transmits a timestamp along with blood sugar level data from the sugar sensor (block 228). Once the transmission is complete, functionality of the sugar device is disabled to conserve power.

Figure 3:
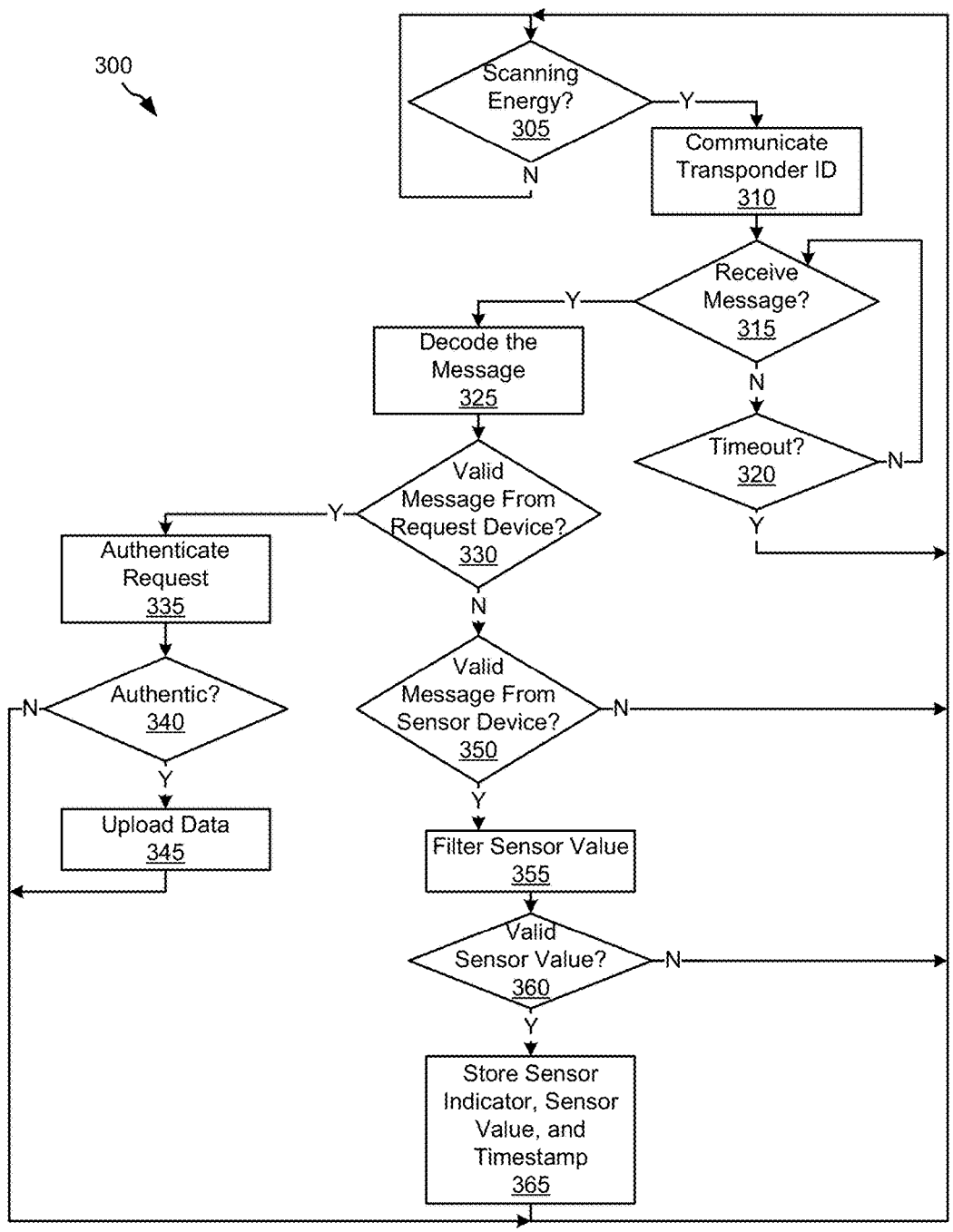
FIG. 3 is a flow diagram showing a method in accordance with some embodiments of the present inventions for gathering patient information from a given sensor using a mobile transponder.

Turning to FIG. 3, a flow diagram 300 shows a method in accordance with some embodiments of the present inventions for gathering patient information from a given sensor using a mobile transponder. Following flow diagram 300, it is determined whether the mobile transponder is receiving scanning energy (e.g., is within a field of RF energy at a frequency expected from a scanning antenna of a sensor device) (block 305). The mobile transponder derives energy from the RF energy field which is used to power components of the mobile transponder. Where the scanning energy is detected (block 305), the mobile transponder transmits a transponder identification (block 310). This transmission when received by a device providing the scanning energy alerts the device to the proximity of a recipient device.

It is then determined whether a message has been received from the sensor device that provided the scanning energy (block 315). Where no message has been received (block 315), it is determined whether a timeout condition has occurred (block 320). Where a timeout condition has not yet occurred (block 320), the process of block 315 is repeated. Alternatively, where a timeout condition has occurred (block 320), the process of clock 305 is repeated.

Otherwise, where a message has been received (block 315), the message is decoded (block 325). The message includes a RQUST field indicating whether the response is a read request from a host requesting information from the mobile transponder, or a write request from a sensor device providing information to be stored in the mobile transponder. Decoding the message includes determining whether it is a write message from a sensor device or a read message from a requesting device. A requesting device may be, for example, a home computer operated by the individual associated with the mobile transponder or a central processing device operated by a health care provider. Based upon the disclosure provided herein, one of ordinary skill in the art will recognize a variety of requesting devices that may be used in relation to different embodiments. Where it is a read message from a host device, the decoding includes comparing a received requestor ID with a set of known requestor IDs maintained in the memory of the mobile transponder. Where the received requestor ID matches one of the known requestor IDs the message is considered a valid message from a requesting device (block 330). Where a valid message from a requesting device has been received (block 330), the request is authenticated using a requestor access code included in the message (block 335). This authentication may use any authentication process known in the art. Where the request is found to be authentic (block 340), all of the data stored on the mobile transponder is transferred to the requesting device (block 345).

Alternatively, where the received message is a not a valid read request (block 330), it is determined whether the message includes a valid write request from a sensor device (block 350). Where decoding has established that the message is from a sensor device (e.g., the RQUST field indicates incoming data), the decoding further includes using a sensor type field to identify the particular type of sensor providing the message. A sensor device may be any device providing information about the individual associated with the mobile transponder such as, for example, a weight device, a sugar device, a blood pressure device, a pulse device, an oxygen device, an exercise machine, or some combination of the aforementioned. A message is considered to be a valid message from a sensor device where the sensor type is recognizable.

Where a valid message from a sensor device is received (block 350), the received sensor data included as part of the message may be filtered to remove any spurious readings (block 355). Such filtering may include any process where information that is likely in error is not stored. As one example, where the sensor type is a weight sensor, a weight data that is twenty-five percent greater or twenty-five percent less than an average of three prior weight readings stored in the mobile transponder may be rejected as an invalid sensor value (block 360). Based upon the disclosure provided herein, one of ordinary skill in the art will recognize a variety of filtering that may be applied to different sensor information in accordance with different embodiments. Further, in some cases no filtering is applied in the mobile transponder, but rather all data is recorded and may be subjected to filtering by a host that receives the data from the mobile transponder. Where a valid sensor value is received (block 360), the sensor indicator, sensor data, and corresponding time stamp are stored to the memory on the mobile transponder (block 365).

Figure 4:
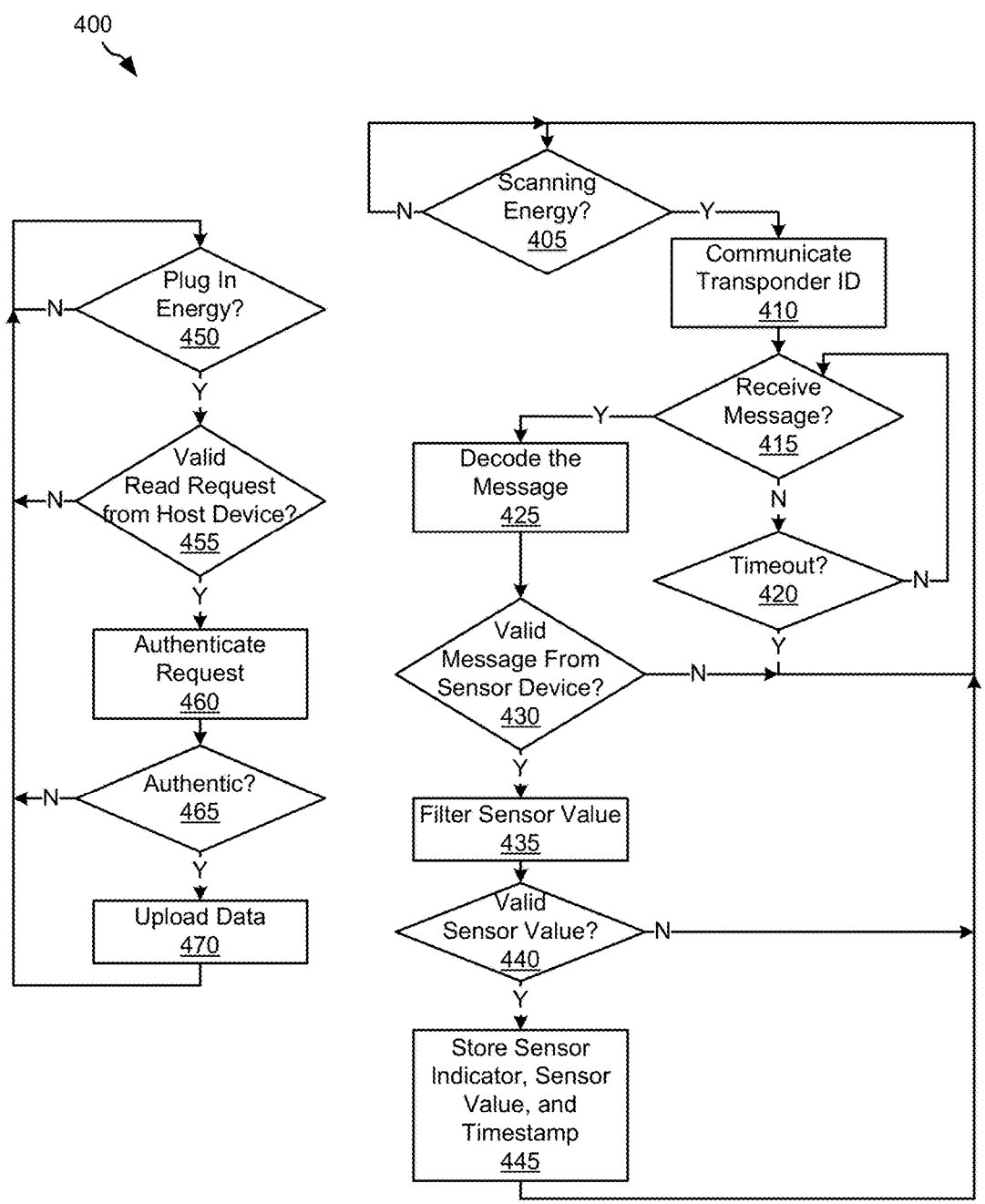
FIG. 4 is a flow diagram showing a method in accordance with various embodiments of the present inventions for uploading patient information from a mobile transponder to a host device.

Turning to FIG. 4, a flow diagram 400 shows a method in accordance with various embodiments of the present inventions for uploading patient information from a mobile transponder to a host device and to uploading information from a sensor device to a mobile transponder. Following flow diagram 400, it is determined whether the mobile transponder is receiving scanning energy (e.g., is within a field of RF energy at a frequency expected from a scanning antenna of a sensor device) (block 405). The mobile transponder derives energy from the RF energy field which is used to power components of the mobile transponder. Where the scanning energy is detected (block 405), the mobile transponder transmits a transponder identification (block 410). This transmission when received by a device providing the scanning energy alerts the device to the proximity of a recipient device.

It is then determined whether a message has been received from the sensor device that provided the scanning energy (block 415). Where no message has been received (block 415), it is determined whether a timeout condition has occurred (block 420). Where a timeout condition has not yet occurred (block 420), the process of block 415 is repeated. Alternatively, where a timeout condition has occurred (block 420), the process of clock 405 is repeated.

Otherwise, where a message has been received (block 415), the message is decoded (block 425). A message received via a device providing scanning energy is considered a write request from a sensor device. The decoding further includes using a sensor type field to identify the particular type of sensor providing the message. A sensor device may be any device providing information about the individual associated with the mobile transponder such as, for example, a weight device, a sugar device, a blood pressure device, a pulse device, an oxygen device, an exercise machine, or some combination of the aforementioned. A message is considered to be a valid message from a sensor device where the sensor type is recognizable.

Where a valid message from a sensor device is received (block 430), the received sensor data included as part of the message may be filtered to remove any spurious readings (block 435). Such filtering may include any process where information that is likely in error is not stored. As one example, where the sensor type is a weight sensor, a weight data that is twenty-five percent greater or twenty-five percent less than an average of three prior weight readings stored in the mobile transponder may be rejected as an invalid sensor value (block 440). Based upon the disclosure provided herein, one of ordinary skill in the art will recognize a variety of filtering that may be applied to different sensor information in accordance with different embodiments. Further, in some cases no filtering is applied in the mobile transponder, but rather all data is recorded and may be subjected to filtering by a host that receives the data from the mobile transponder. Where a valid sensor value is received (block 445), the sensor indicator, sensor data, and corresponding time stamp are stored to the memory on the mobile transponder (block 445).

In parallel, it is determined whether the mobile transponder is receiving plug in energy (block 450). Plug in energy is received by the mobile transponder when the mobile transponder is connected to a host device via a plug in connector such as, for example, a USB connector. Where plug in energy is being received (block 450), it is determined whether a valid read request has been received from a host via a plug in connector (block 455). Determination of a valid read request is done by comparing a received requestor ID with a set of known requestor IDs maintained in the memory of the mobile transponder. Where the received requestor ID matches one of the known requestor IDs the message is considered a valid message from a host device (block 455).

Where a valid read request from a host device has been received (block 455), the request is authenticated using a requestor access code included in the message (block 460). This authentication may use any authentication process known in the art. Where the request is found to be authentic (block 465), all of the data stored on the mobile transponder is transferred to the requesting host device (block 470).

Figure 5:
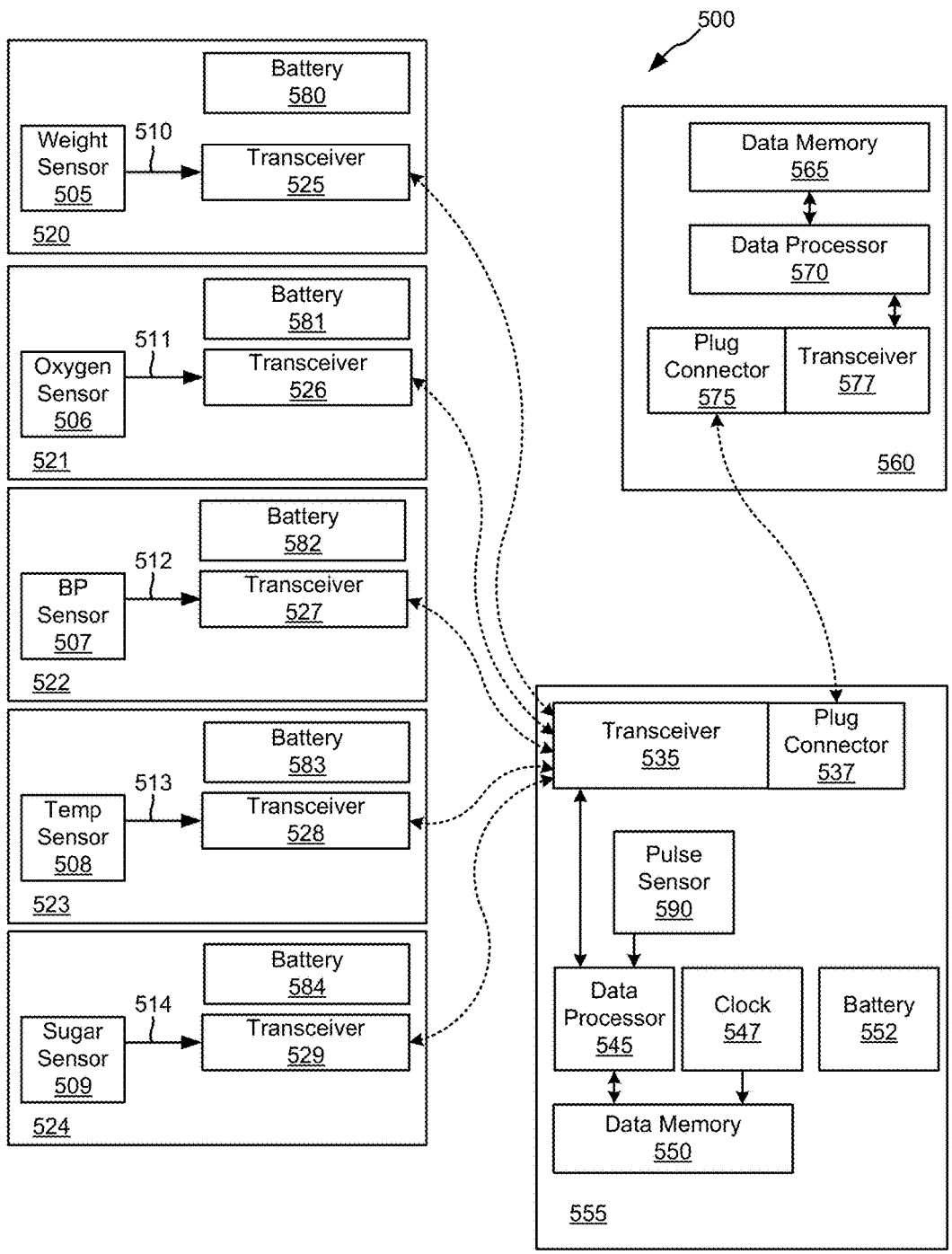
FIG. 5 shows another system including a mobile transponder powered using an internal battery operable to gather sensor information from one or more sensors in accordance with particular embodiments of the present inventions.

Turning to FIG. 5, a system 500 including a mobile transponder 555 powered using an internal battery 552 operable to gather sensor information from one or more sensors in accordance with particular embodiments of the present inventions. System 100 also includes a host device 560 for offloading and processing data from mobile transponder 555.

Mobile transponder 555 includes a transceiver circuit 535 that receives sensor data transmitted from one or more devices 520, 521, 522, 523, 524 over a short range, and transfers the received data to a data processor 545 where it is parsed and processed. This parsing and processing may include, but is not limited to, determining the type of sensor device that provided the response, filtering the received sensor data, and where appropriate, storing the received sensor data a data memory 550 along with a timestamp created based upon a clock circuit 547. In some cases, data memory 550 is a flash RAM. In other cases, data memory 550 is a static RAM. In yet other cases, data memory 550 is a combination of flash RAM and static RAM. The timestamp may indicate a date and time the data from the particular sensor device was received. As one example, the data received from the sensor device via transceiver 535 may include the fields set forth below in relation to Table 3.

TABLE 3

| Sensor Type | Sensor Data |
| --- | --- |

The sensor type field may be a ten bit field indicating a particular sensor type (e.g., weight, pulse, oxygen, blood pressure, temperature, blood sugar). As another example, the sensor type may be a particular type of exercise machine.

Based upon the disclosure provided herein, one of ordinary skill in the art will recognize a variety of sensor types that may be used in relation to different embodiments. The sensor data field may be a sixty-four bit field indicating the measurement data. Thus, for example, where the sensor type is a weight sensor the sensor data may be the measured weight. As another example, where the sensor type is a treadmill the sensor data may be an exercise time, distance, and approximate calorie count. The received sensor data may be stored in any format in data memory 550 that allows it to be retrieved at a later date.

Mobile transponder 555 additionally includes a plug connector 537 that allows for transferring data to and from mobile transponder via a wired connection using, for example, a USB interface protocol. Based upon the disclosure provided herein, one of ordinary skill in the art will recognize a variety of wired data transfer protocols that may be used in relation to different embodiments of the present inventions. Further, mobile transponder 555 includes a pulse sensor device 590 that is capable of sensing the pulse of an individual associated with mobile transponder 555. Any pulse sensor device capable of sensing the pulse of an individual may be used in relation to embodiments. Pulse sensor device 590 periodically provide pulse data to data processor 545 which filters the pulse data and stores the filtered pulse data in data memory 550 along with a time stamp from clock 547.

Weight sensor device 520 includes: a weight sensor circuit 505 that operates to indicate the weight of an object placed on weight sensor device 520, a battery 580 that powers weight sensor device 520, and a transceiver 525 operable to transmit weight data 510 over a short range (e.g., less than ten feet). In operation, a subject to be measured (not shown) steps on weight sensor device 520. In response, weight sensor circuit 505 generates weight data 510 indicating the weight of the subject. Where weight data 510 exceeds a threshold value (e.g., five pounds) and is stable (i.e., has remained unchanged for ten seconds), transceiver 525 is placed in a wake mode. In the wake mode, transceiver 525 transmits the weight data 510. The transmission may be done over any short range transmission protocol known in the art. Once the data is transmitted, transceiver 525 is returned to the sleep mode.

Oxygen sensor device 521 includes: an oxygen sensor circuit 506 that operates to indicate a blood oxygen level of the subject using oxygen sensor device 521, a battery 581 that powers oxygen sensor device 521, and a transceiver 526 operable to transmit oxygen data 511*a*. In operation, a subject to be measured (not shown) deploys pulse/oxygen sensor device 521. In response, oxygen sensor circuit 506 generates oxygen data 511 indicating a pulse and a blood oxygen level of the subject using oxygen sensor device 521. Where oxygen data 511 exceeds a threshold value (e.g., pulse greater than 30 beats per minute) and is stable (i.e., has remained unchanged for ten seconds), transceiver 526 is placed in a wake mode. In the wake mode, transceiver 526 transmits the oxygen data 511. Once the data is transmitted, transceiver 526 is returned to the sleep mode.

Blood pressure sensor device 522 includes: a blood pressure sensor circuit 507 that operates to indicate a blood pressure of the subject using blood pressure sensor device 522, a battery 582 that powers blood pressure sensor device 522, and a transceiver 527 operable to transmit systolic and diastolic blood pressure data 512. In operation, a subject to be measured (not shown) deploys blood pressure sensor device 522. In response, blood pressure sensor circuit 507 generates systolic and diastolic blood pressure data 512 indicating a pulse and a blood oxygen level of the subject using blood pressure sensor device 522. Where systolic and diastolic blood pressure data 512 exceeds a threshold value (e.g., systolic blood pressure greater than 20 mmHg) and is stable (i.e., has remained unchanged for ten seconds), transceiver 527 transmits the systolic and diastolic blood pressure data 512. Once the data is transmitted, transceiver 527 is returned to the sleep mode.

Temperature sensor device 523 includes: a temperature sensor circuit 508 that operates to indicate a temperature of the subject using temperature sensor device 523, a battery 583 that powers temperature sensor device 523, and a transceiver 528 operable to transmit temperature data 513. In operation, a subject to be measured (not shown) deploys temperature sensor device 523. In response, temperature sensor circuit 508 generates temperature data 513 indicating a temperature of the subject using temperature sensor device 523. Where temperature data 513 exceeds a threshold value (e.g., temperature greater than 86 degrees F.) and is stable (i.e., has remained unchanged for ten seconds), transceiver 528 transmits the temperature data 513. Once the data is transmitted, transceiver 528 is returned to the sleep mode.

Sugar sensor device 524 (e.g., a glucometer) includes: a sugar sensor circuit 508 that operates to indicate a blood sugar level of the subject using sugar sensor device 524, a battery 584 that powers sugar sensor device 524, and a transceiver 529 operable to transmit sugar data 514. In operation, a subject to be measured (not shown) deploys sugar sensor device 524. In response, sugar sensor circuit 509 generates sugar data 514 indicating a blood sugar level of the subject using sugar sensor device 524. Where sugar data 514 exceeds a threshold value (e.g., sugar greater than 500 mg/dL) and is stable (i.e., has remained unchanged for ten seconds), transceiver 529 transmits the sugar data 514. Once the data is transmitted, transceiver 529 is returned to the sleep mode.

A host device 560 includes: a plug connector 575, a transceiver 577, a data processor 570, and a data memory 565. Transceiver 577 either wirelessly or via plug connector 575 transmits commands to mobile transponder 555. The commands may be to download programs to mobile transponder 555 or to request data from mobile transponder 555. In response to a read data received from host 560, mobile transponder 555 uploads all measure data and corresponding timestamps maintained in data memory 550 to host device 560. The received uploaded data is provided to a data processor 570 that both processes the received data and stores the received data to a data memory 565.

Figure 6:
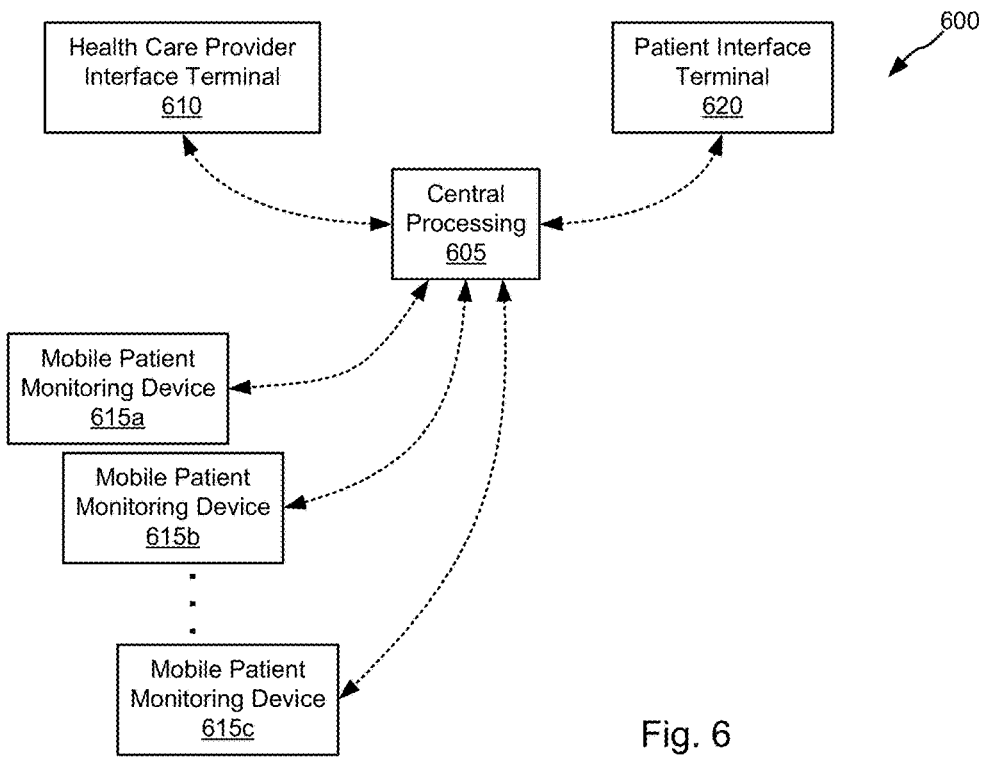
FIG. 6 shows another system including a central processing device operable to upload and download information to/from a mobile transponder in accordance with some embodiments of the present inventions.

Turning to FIG. 6, another system 600 including a central processing device 605 operable to upload and download information to/from various mobile patient devices 615 is shown in accordance with some embodiments of the present inventions. Central processing device 605 may be, but is not limited to, a computer server database accessible both locally and remotely and capable of processing various commands in relation to mobile patient devices 615, a physician interface terminal 610, and/or a patient interface terminal 620. In some cases, central processing device 605 may be wirelessly connectable to mobile patient monitoring devices 615 using a connection similar to the connection between mobile transponder 155 and host 160 discussed above in relation to FIG. 1. In such a case, host 160 may be the same device as central processing device. In other cases, central processing device 605 may be connectable to mobile patient monitoring devices 615 via a network interface. In such a configuration, mobile patient monitor device 615 includes, for example, both host 160 and mobile transponder 155 of FIG. 1 where data is transferred to host 160 from mobile transponder 155, and then from host 160 to central processing device 605 via a network connection. As an alternative, mobile patient monitor device 615 includes, for example, both host 560 and mobile transponder 555 of FIG. 5 where data is transferred to host 560 from mobile transponder 555, and then from host 560 to central processing device 605 via a network connection. In yet other cases, central processing device 605 may be directly connectable to mobile patient monitoring devices 615 via a wired interface interface. In such a configuration, a wire is connected between a co-located mobile patient monitoring device 615 and central processing device 605.

Mobile patient device 615 may be a device worn or carried by a patient that electronically gathers various information about the patient available from one or more wireless enabled sensor devices. In some embodiments, mobile patient device 615 may be implemented and operate similar to that discussed above as mobile transponders in relation to FIGS. 1 and 5. Based upon the disclosure provided herein, one of ordinary skill in the art will recognize a variety of implementations of mobile patient devices that may be used in relation to different embodiments.

A health care provider interface terminal 610 may be any computer or computer interface that allows a health care provider to provide commands to central processing device 605 and/or receive data from central processing device 605. A patient interface terminal 620 may be any computer or computer interface that allows a patient to provide commands to central processing device 605 and/or receive data from central processing device 605.

Figure 7:
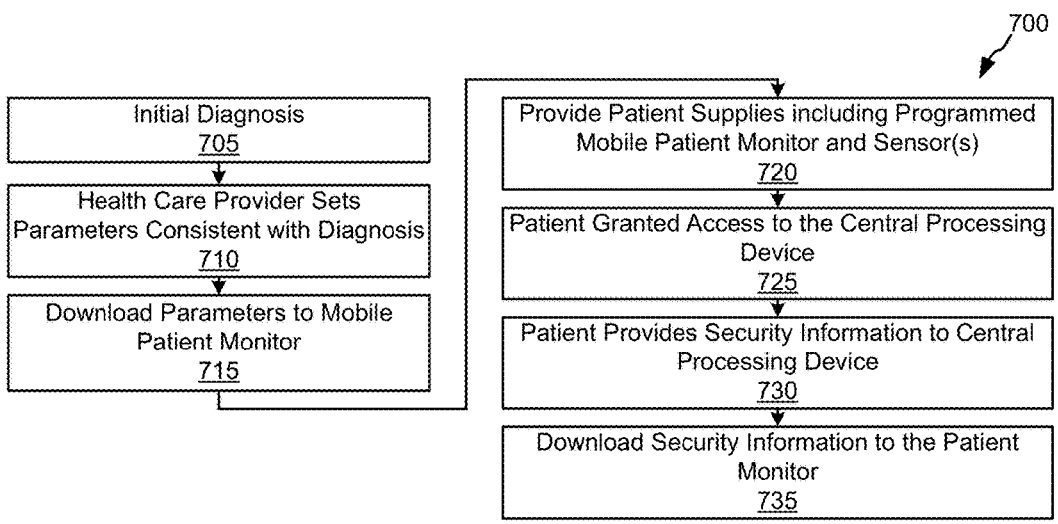
FIG. 7 is a flow diagram showing a method in accordance with various embodiments of the present inventions for deploying a patient device.

Turning to FIG. 7, a flow diagram 700 shows a method in accordance with various embodiments of the present inventions for deploying a patient device. Following flow diagram 700, an initial diagnosis of a patient's condition is made by a health care provider (block 705). This diagnosis may be done during a standard patient visit where various vitals of the patient are measured, a physician considers the vitals and a patient's medical history, and the physician diagnoses a condition of the patient. The health care provider then sets a variety of parameters that will be used in monitoring the patient over a period that the patient is away from the medical office (block 710). For example, if the diagnosis is heart failure, the parameters may include weight data parameters, pulse data parameters, and oxygen level parameters. Based upon the disclosure provided herein, one of ordinary skill in the art will recognize a variety of parameters that may be monitored depending upon the particular diagnosis. These parameters are loaded into a central processing device using a health care provider interface terminal, and then subsequently downloaded from the central processing device to a mobile patient monitoring device (or a host device used by the patient) (block 715).

The patient is provided with supplies to monitor their condition including, but not limited to, the programmed patient monitoring device and one or more sensor devices that automatically communicate with the mobile patient monitoring device (block 720). In addition, the patient is granted access to the central processing device (block 725) where they may provide security information to the central processing device via a patient interface terminal (block 730). This may include, but is not limited to, providing patient unique authentication information that will allow the central processing device to authenticate itself to the mobile patient monitoring device allowing the central processing device to obtain data gathered by the mobile patient monitoring device. This authentication information is then downloaded to the mobile patient monitoring device (block 735). At this juncture, the patient is prepared to use the combination of the mobile patient monitoring device to automatically gather vitals about the patient and make those vitals available to a health care provider via the central processing device.

Figure 8:
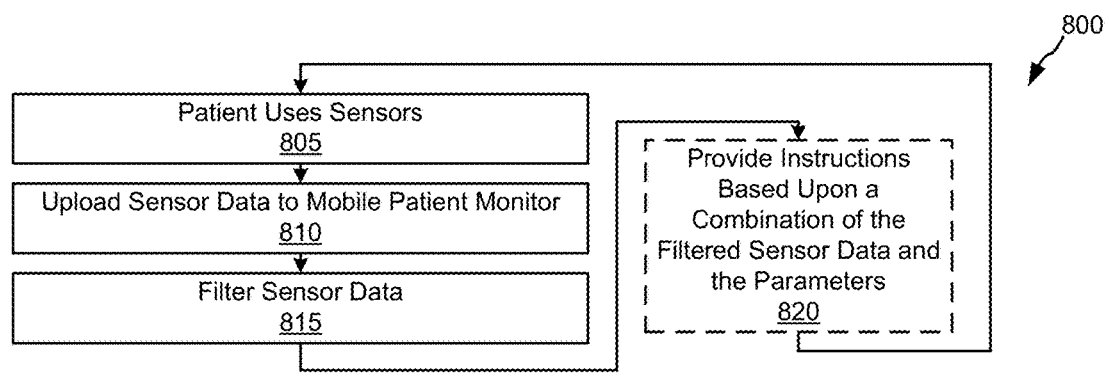
FIG. 8 is a flow diagram showing a method in accordance with various embodiments of the present inventions for utilizing a patient device.

Turning to FIG. 8, a flow diagram 800 shows a method in accordance with various embodiments of the present inventions for utilizing a mobile patient device. Following flow diagram 800, the patient uses one or more sensors while either wearing the mobile patient device or having the mobile patient device near their person (block 805). Using the sensors can include, but is not limited to: stepping on a scale that is operable similar to the weight sensor device discussed above in relation to FIG. 1, taking a blood pressure reading using a blood pressure sensor device that is operable similar to the blood pressure sensor device discussed above in relation to FIG. 1, taking a blood oxygen and pulse reading using a pulse/oxygen sensor device that is operable similar to the pulse/oxygen sensor device discussed above in relation to FIG. 1, taking a blood sugar reading using a Glucometer™ that is operable similar to the sugar sensor device discussed above in relation to FIG. 1, taking a temperature reading using a thermometer that is operable similar to the temperature sensor device discussed above in relation to FIG. 1, and/or using an exercise machine that is operable to wirelessly report various statistics regarding the health status of the patient.

The measurement data and timestamp data generated by the one or more sensors is uploaded to the mobile patient monitoring device (block 810). The received data is filtered (block 815). The filtering may include removing any measurement data that is most likely in error. For example, where the newly measured weight of the patient is more than twenty pounds greater or less than an average weight of the preceding three days it is most likely a spurious reading and as such is removed by the filtering process. A similar filtering approach may be applied to other measurement data. In some cases, no filtering is applied. Also, it should be noted that in some cases the filtering is done as a post process by a host or the central processing device that receives the raw data from the mobile patient monitoring device. Instructions are then provided based upon a combination of the filtered (or raw) sensor data and the parameters provided by the health care provider (block 820). This process of providing instructions is shown in a dashed line as an example of the process is provided in greater detail below in relation to FIG. 10. The aforementioned post filtering may be done where a host or the central processing device is processes the data and provides instructions to the patient discussed in relation to block 820.

Figure 9:
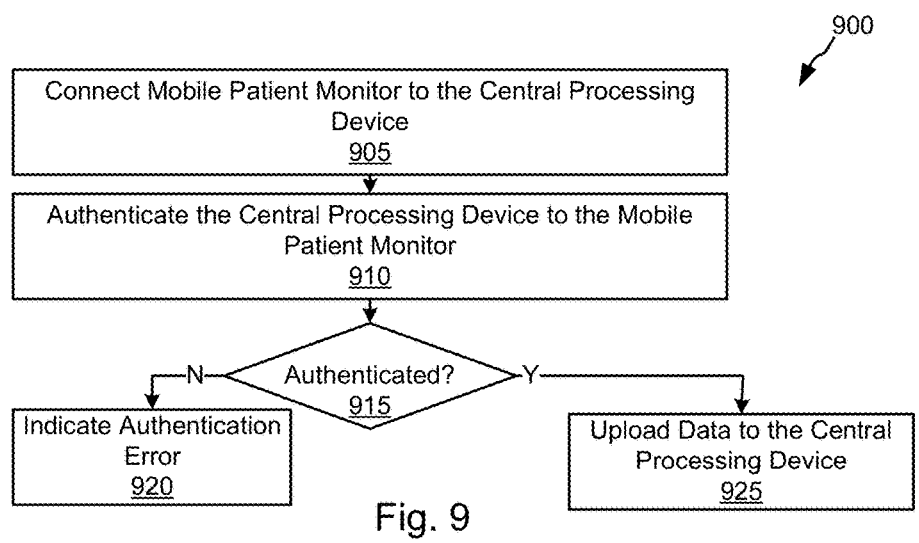
FIG. 9 is a flow diagram showing a method in accordance with various embodiments of the present inventions for offloading data from a patient device.

Turning to FIG. 9, a flow diagram shows a method in accordance with various embodiments of the present inventions for offloading data from a mobile patient device. It should be noted that while flow diagram shows a method for offloading data from the mobile patient device to a central processing device, the same process may be used for offloading data to a host device used by a patient. Following flow diagram 900, the mobile patient monitoring device is connected to the central processing device (block 905). This may include, for example, bringing the mobile patient monitoring device within wireless range of the central monitoring device where the offload is accomplished wirelessly, or by using a wire to connect the mobile patient monitoring device to the central monitoring device where any wired interface protocol may be used for communication between the devices.

The central processing device is then authenticated to the mobile patient monitoring device (block 910). This may include providing security information originally provided to the central processing device (see blocks 730-735 of FIG. 7) from the central processing device to the mobile patient monitoring device. Using this security information, the mobile patient monitoring device determines whether access is to be granted to the central processing device (block 915). Where access is not granted (block 915), an authentication error is indicated (block 920). Alternatively, where access is granted (block 915), a read request from the central processing device is serviced and all data related to the patient is uploaded to the central processing device (block 925).

Figure 10:
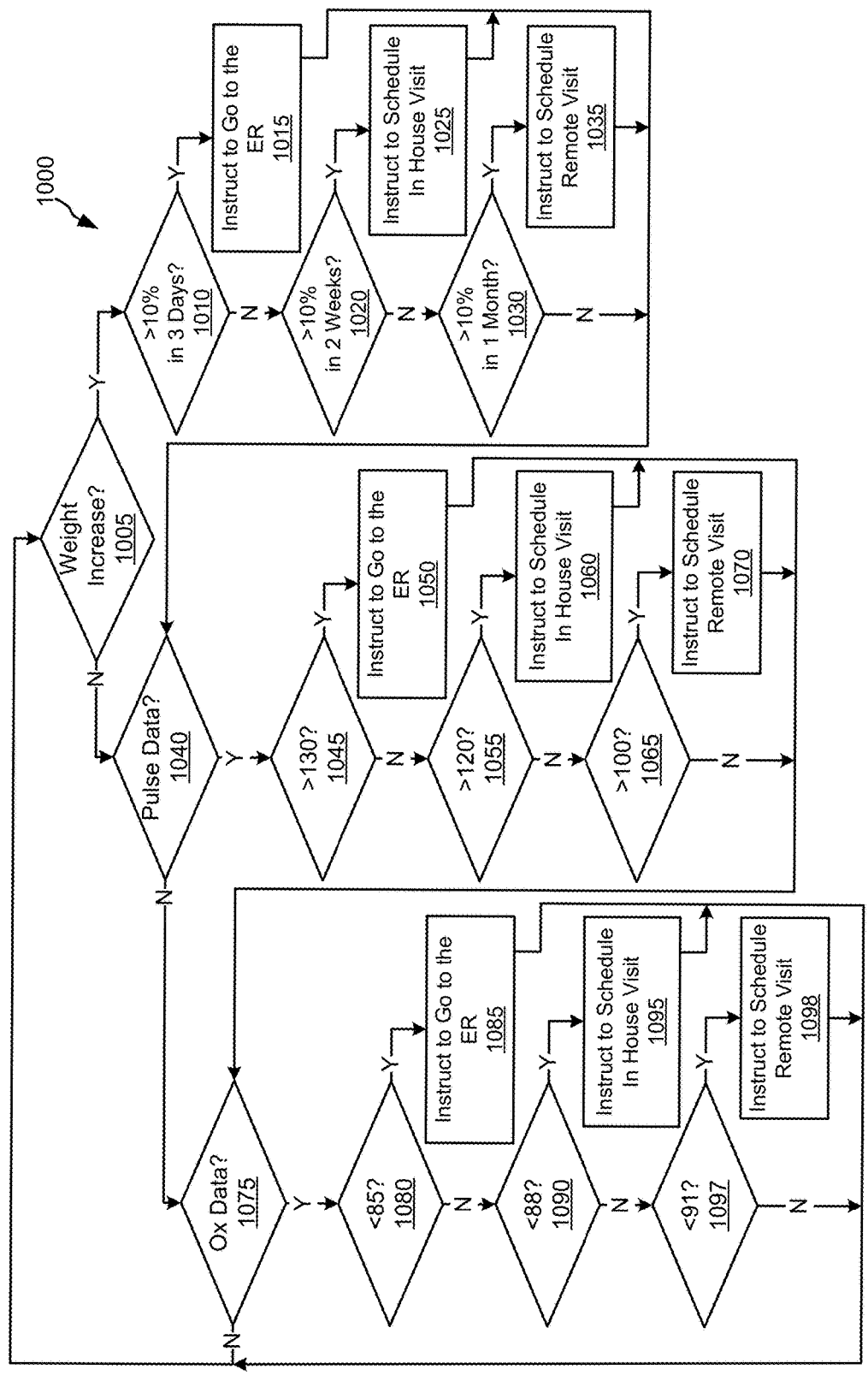
FIG. 10 is a flow diagram showing an example of healthcare delivery using a patient device in accordance with various embodiments of the present inventions.

Turning to FIG. 10, a flow diagram 1000 shows a detailed example of providing instructions based upon a combination of filtered sensor data and health care provider parameters (i.e., block 820 of FIG. 8) is shown in accordance with some embodiments where the initial diagnosis (i.e., block 705 of FIG. 7) is heart disease. Following flow diagram 1000, a host using the sensor data offloaded from the mobile patient monitoring determines whether the data indicates an increase in weight (block 1005). Where an increase in weight is identified (block 1005), it is determined whether the increase is greater than a ten percent increase over a course of three days or less (block 1010). Where the increase is greater than ten percent over a course of three days or less (block 1010), an instruction is provided to the patient to go to a local emergency room for further assistance (block 1015). Alternatively, where the increase is not greater than ten percent over a course of three days or less (block 1010) and is greater than ten percent over a course of two weeks or less (block 1020), an instruction is provided to the patient to contact their health care provider to make an in-person appointment (block 1025). Alternatively, where the increase is not greater than ten percent over a course of two weeks or less (block 1020) and is greater than ten percent over a course of one month or less (block 1030), an instruction is provided to the patient to contact their health care provider to make a remote video visit via the Internet (block 1035). Otherwise where a weight gain of more than ten percent in less than a month is not found in the sensor data (block 1030), no patient instruction is issued.

Where pulse data is available (block 1040), it is determined whether the pulse data is greater than one hundred thirty (130) (block 1045). Where a pulse of greater than one hundred thirty (130) was measured (block 1045), an instruction is provided to the patient to go to a local emergency room for further assistance (block 1050). Alternatively, where a pulse of less than one hundred thirty (130) and greater than one hundred twenty (120) was measured (block 1055), an instruction is provided to the patient to contact their health care provider to make an in-person appointment (block 1060). Alternatively, where a pulse of less than one hundred twenty (120) and greater than one hundred (100) was measured (block 1065), an instruction is provided to the patient to contact their health care provider to make a remote video visit via the Internet (block 1070). Otherwise where no pulse measurement greater than one hundred occur, no patient instruction is issued.

Where oxygen data is available (block 1075), it is determined whether the oxygen data is less than eighty five (85) (block 1080). Where an oxygen measurement of less than eighty five (85) is recorded (block 1080), an instruction is provided to the patient to go to a local emergency room for further assistance (block 1085). Alternatively, where an oxygen measurement greater than eighty five (85) and less than eighty eight (88) was measured (block 1090), an instruction is provided to the patient to contact their health care provider to make an in-person appointment (block 1095). Alternatively, where an oxygen measurement greater than eighty five (88) and less than ninety one eight (91) was measured (block 1097), an instruction is provided to the patient to contact their health care provider to make a remote video visit via the Internet (block 1098). Otherwise where no oxygen measurement less than ninety one eight (91) occur, no patient instruction is issued.

While the systems and methods herein may be used in relation to patients with heart failure, many other diagnosis may also be supported. For example, the systems and methods set forth herein may be used in relation to supporting a patient with diabetes. Patients with diabetes would be able to record their blood glucose using a monitor connected to RFID. Following an initial appointment with a primary care practitioner where the practitioner set insulin and glucose parameters for the patient, the patient would be sent home with a glucometer connected to their mobile device. Notifications would be sent to the patient's mobile device when it was time to take a glucose. The patient then takes their glucose using a glucometer connected to RFID. A notification is sent to the patient's mobile device with how much insulin the patient would need to administer to themselves. Patients would be able to record how many carbs they eat and receive notifications on their mobile device regarding how much insulin to administer for that many carbs. Parameters would also be set for low blood glucose. The primary care practitioner would set parameters and instructions for the patient regarding when the patient could simply eat carbohydrates and when the patient needed to go to the emergency department. Notifications would be sent to the patient's mobile device with instructions on when to go to the hospital for glucose that is too high or too low. Examples of parameters: a blood glucose of greater than 500 would trigger a notification to go to the emergency department. A blood glucose of 400-500 would trigger a notification to make an in office appointment with the primary care provider, and a blood glucose reading of 350-400 would trigger a notification to make a video appointment with the primary care provider. A blood glucose of 141-350 would trigger a notification to give insulin according to parameters set by the primary care provider. A blood glucose reading of 71-140 would trigger a notification that the reading does not require action other than to check the glucose the next time it needs to be checked according to parameters set by the primary care provider. A blood glucose of 41-70 would notify the patient to consume carbohydrates and recheck their glucose in 2 hours (or another time frame as specified by the primary care provider). A blood glucose of below 41 would trigger a notification that the patient needed to go to the emergency department.

As yet another example, systems and methods discussed herein may be used to support patients with renal failure. Along with their multiple dialysis appointments every week, patients are also required to frequently have appointments with a primary care provider. With this system, the patient would be able to monitor and record their urine output. Every time the patient urinates, they simply record the amount in the system. Notifications are sent to the patient regarding parameters set by the primary care provider. For example, if the patient has a urine output of less than 100 milliliters in a 4 hour period, a notification is sent to the patient to either record an output that has not been recorded or go to the emergency department for a low urine output. Pts who had less than 1200 milliliters of urine output in 12 hours would receive a notification to get an in office appointment with the primary care provider, and pts who had a urine output of less than 2400 milliliters in a 24 hour period would receive a notification to make a video appointment with the primary care provider. The patient could also use the system mentioned in FIG. 10 regarding weight monitoring to monitor fluid retention and allow the primary care provider to monitor their weight in real time. For example: patients who gained more than 5 pounds in a 3 day period would receive a notification to go to the emergency department, patients who gained 10 pounds in a two week period would receive a notification to make an in office appointment with the primary care provider, and patients who had weight gain of 25 pounds in two weeks would trigger a notification to make a video appointment with the primary care provider.

It should be noted that use of the systems and methods describe herein are not limited to supporting patients with chronic conditions. Systems and methods discussed herein may be used in relation to patients recently discharged from a hospital to support them in following recovery instructions. This would allow for discharging patients earlier and allowing them to care for themselves at home using instructions provided from the system.

For example, patients that are discharged with Jackson Pratt drains could use this system to keep track of drain output. The patient would empty the drain and record how much output there is. The patient would then take a picture of the output so the primary care provider could monitor color and changes in character of output. Upon discharge from the hospital, the provider would set parameters for the patient in amount of output required to remove the drain. After the patient records output that drops below the parameters set by the primary care provider, a notification is sent to the patient to make an appointment with the primary care provider to have the drain removed. Currently, patients are given a piece of paper with a grid to handwrite outputs on and are told to make an appointment to have the drain removed once the output reaches a certain level. This system would allow the primary care provider to monitor outputs in real time as well as monitor the character of the output, not just the numbers. This system only requires the technology needed to record outputs, take pictures of output, and receive notifications.

As another example, many patients are discharged from the hospital with wounds that are difficult to manage. Currently, many patients are sent home with prescriptions for home healthcare professionals to come to their home and care for the wound. Many times, the patient and family are also required to do dressing changes. This system could be used to monitor wound care. When doing the dressing change, the patient would take pictures of the wound allowing the primary care provider to monitor the wound remotely every time the patient does a dressing change. This would decrease the need to pay for home health professionals to monitor the wound. The primary care provider would then be able to send notifications to the patient regarding the need for an in office appointment for the wound.

Figure 11A:
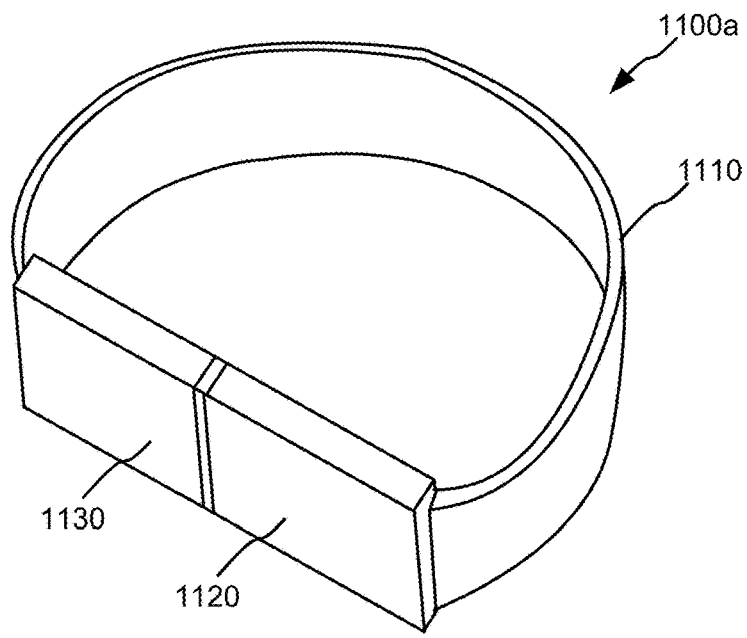
FIG. 11a-11b show an example mobile transponder in both a connected and unconnected position in accordance with some embodiments of the present inventions.
Figure 11B:
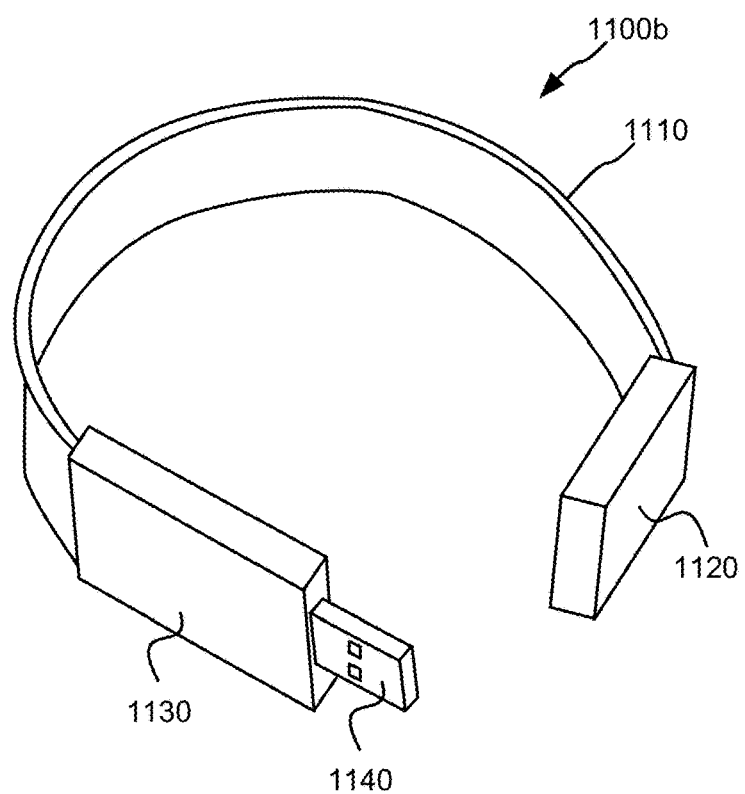

Turning to FIGS. 11a-11b, an example of a mobile transponder 1100 is shown in both a connected (FIG. 11a) and unconnected (FIG. 11b) position in accordance with some embodiments of the present inventions. As shown mobile transponder 1100 is suitable for wearing around the wrist or ankle of an individual (not shown) being monitored. Mobile transponder 1100 includes a strap 1110 that attaches to both a first side 1120 of a buckle and a second side 1120 of the buckle. When disconnected (FIG. 11a), a plug in connector 1140 (e.g., USB connector) second side 1130 of the buckle. It should be noted that other types of connectors may be used in place of the buckle shown, and that in some cases a plug in connector may be included that can be exposed without disconnecting the mobile transponder from around the limb of an individual.

Figure 12:
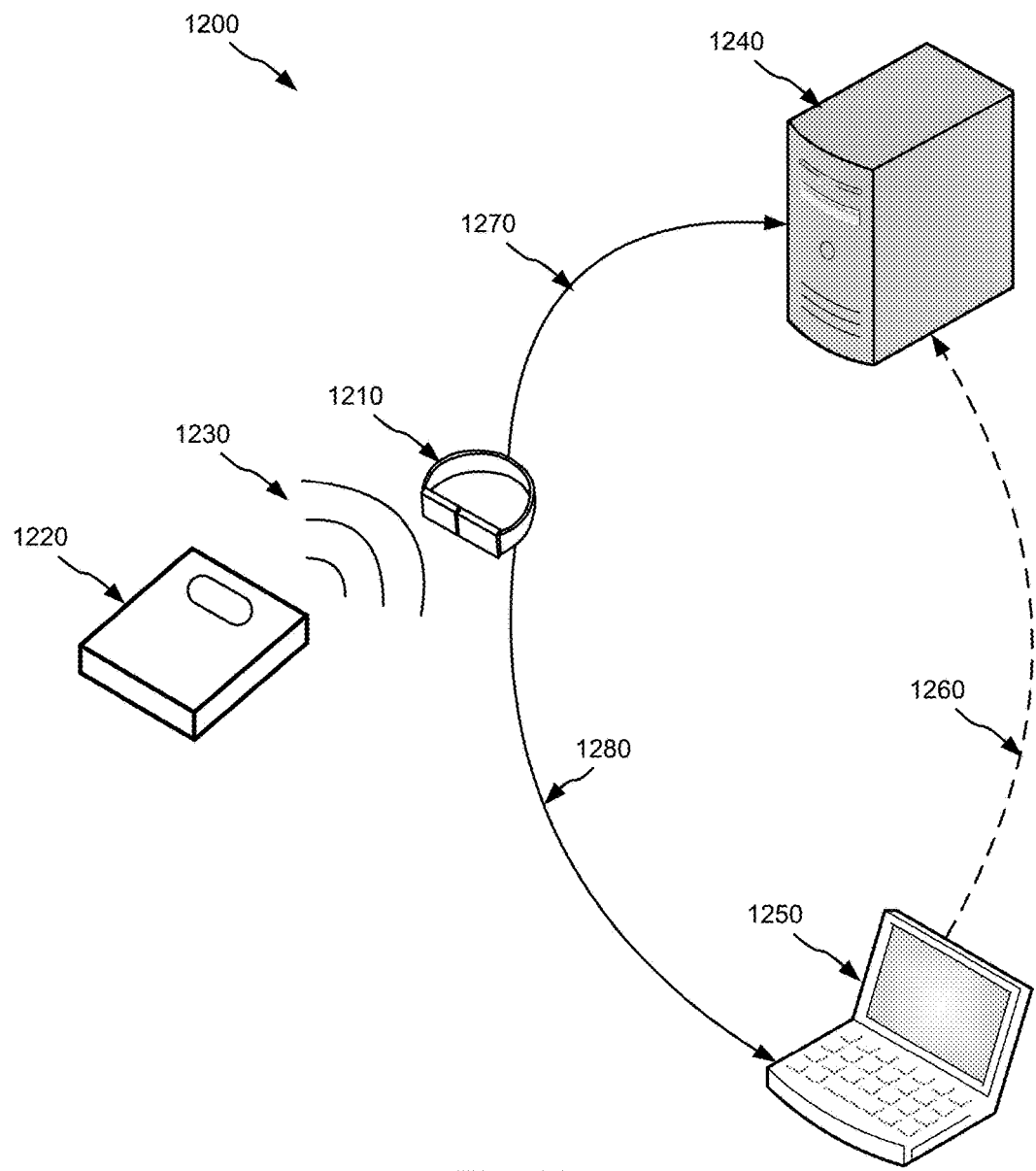
FIG. 12 shows a system including a mobile transponder, weight device, home computer, and central processing server in accordance with some embodiments of the present inventions.

Turning to FIG. 12, a system 1200 is shown that includes: a mobile transponder 1210 that would typically be worn or carried by an individual (not shown) that is being monitored, a weight device 1220 (i.e., a scale), a home computer 1250, and central processing server 1240 that would typically be deployed at the location of a health care provider. In some cases, mobile transponder 1210 may be implemented similar to mobile transponder 155 discussed above in relation to FIG. 1 or mobile transponder 555 discussed above in relation to FIG. 5.

When the individual being monitored steps on weight device 1220 their weight is measured. With the weight registering as greater than some threshold value, weight device 1220 generates an RFID field 1230 which is electromagnetic energy at a specified frequency. In some cases, RFID field 1230 has an effective (i.e., it will provide enough energy to support communication with mobile transponder) range of less than thirty feet. In other cases, RFID field 1230 has an effective (i.e., it will provide enough energy to support communication with mobile transponder) range of less than twenty-two feet. In yet other cases, RFID field 1230 has an effective (i.e., it will provide enough energy to support communication with mobile transponder) range of less than eight feet.

Mobile transponder 1210 receives RFID field 1230 when it is within a short distance (i.e., a distance greater than the distance from weight device 1220 to mobile transponder 1210 when the individual wearing mobile transponder 1210 is on weight device 1220) from weight device 1220. Mobile transponder 1210 is powered by energy derived from RFID field 1230, and using this power communicates a presence or ID signal which is received by weight device 1220. Having established communication, weight device 1220 transmits the weight measured for the individual to mobile transponder 1210 which stores the received data to a memory included in mobile transponder 1210.

At some point, mobile transponder 1210 may be physically connected to either home computer 1250 via a wire 1280 or central processing server 1240 via a wire 1270. In some cases, the connection may be a USB protocol connection. At this point data stored in mobile transponder 1210 may be uploaded to the respective one of home computer 1250 or central processing server 1240. Additionally, data may be uploaded from home computer 1250 to central processing server 1240 via a network interface 1260.

In conclusion, the invention provides novel systems, devices, methods and arrangements for obtaining and processing patient data. While detailed descriptions of one or more embodiments of the invention have been given above, various alternatives, modifications, and equivalents will be apparent to those skilled in the art without varying from the spirit of the invention. For example, while some embodiments discuss a mobile transponder wearable or attachable to an individual, it should be understood that the individual may be a human, another animal, or an object. Therefore, the above description should not be taken as limiting the scope of the invention, which is defined by the appended claims.

What is claimed is:

1. A patient data gathering system, the patient data gathering system comprising:
   a sensor device operable to:
      generate a measurement value corresponding to a physical characteristic of an individual;

generate a radio frequency field, wherein the radio frequency field has enough energy to power a mobile transponder associated with the individual; and transmit a message including the measurement value.

2. The patient data gathering system of claim 1, the patient data gathering system further comprising:
the mobile transponder associated with the individual and including a memory, wherein the mobile transponder is operable to:
generate power from the radio frequency field;
receive the message; and
store a data set to the memory, wherein the data set is derived from the message.

3. The patient data gathering system of claim 2, wherein the physical characteristic of the individual is a first characteristic of the individual, and wherein the mobile transponder further includes a measurement circuit operable to measure a second physical characteristic of the individual.

4. The patient data gathering system of claim 3, wherein the measurement circuit of the mobile transponder includes at least one circuit selected from a group consisting of: a blood pressure monitor circuit operable to detect a blood pressure of the individual, a weight sensor circuit operable to detect a weight of the individual, a pulse/oxygen sensor circuit operable to detect at least one of a pulse and an oxygen level of the individual, a temperature sensor circuit operable to detect a temperature of the individual, a blood glucose sensor circuit operable to detect a blood glucose level of the individual, and an exercise device circuit operable to detect one or more of an exercise time, an exercise distance, and an exercise calorie value.

5. The patient data gathering system of claim 2, wherein the radio frequency field has a range of less than eight feet in which the radio frequency signal provides sufficient energy to support communication with the mobile transponder.

6. The patient data gathering system of claim 5, wherein the radio frequency signal has a range of less than four feet in which the radio frequency signal provides sufficient energy to support communication with the mobile transponder.

7. The patient data gathering system of claim 2, wherein the mobile transponder includes a device identification, and wherein the mobile transponder is further operable to transmit the device identification upon generating power from the radio frequency signal.

8. The patient data gathering system of claim 2, wherein the mobile transponder includes a strap operable to extend around the limb of the individual.

9. The patient data gathering system of claim 2, wherein the mobile transponder includes a plug-in connector operable to accept a physical connection to a port of at least one of a central processing server and a home computer.

10. The patient data gathering system of claim 1, wherein the sensor device includes:
a sensor circuit operable to generate the measurement value; and
a scanning antenna operable to generate the radio frequency field, and wherein the scanning antenna is switched from a sleep mode to a wake mode when the measurement value exceeds a threshold value, and wherein the sleep mode uses less power than the wake mode.

11. The patient data gathering system of claim 1, wherein the sensor device includes:
a scanning antenna operable to generate the radio frequency field; and
a transceiver operable to transmit the measurement data; and
wherein the scanning antenna and the transceiver are switched from a sleep mode to a wake mode when the measurement value exceeds a threshold value, and wherein the sleep mode uses less power than the wake mode.

12. The patient data gathering system of claim 1, wherein the sensor device is selected from a group consisting of: a weight sensor device including a weight sensor circuit, a pulse/oxygen sensor device including a pulse and oxygen sensor circuit, a blood pressure sensor device including a blood pressure sensor circuit, a temperature sensor device including a temperature sensor circuit, a blood glucose sensor device including a blood glucose sensor circuit, and an exercise device.

13. A patient data gathering system, the patient data gathering system comprising:
a mobile transponder associated with an individual and including a memory, wherein the mobile transponder is operable to:
generate power from a radio frequency signal;
receive a message via a wireless communication link, wherein the message includes a measurement value corresponding to a physical characteristic of the individual; and
store a data set to the memory, wherein the data set is derived from the message including the measurement value.

14. The patient data gathering system of claim 13, the patient data gathering system further comprising:
a sensor device operable to:
generate the measurement value corresponding to the physical characteristic of the individual;
generate the radio frequency signal; and
transmit the message including the measurement value.

15. The patient data gathering system of claim 14, wherein the sensor device includes:
a sensor circuit operable to generate the measurement value; and
a scanning antenna operable to generate the radio frequency signal, and wherein the scanning antenna is switched from a sleep mode to a wake mode when the measurement value exceeds a threshold value, and wherein the sleep mode uses less power than the wake mode.

16. The patient data gathering system of claim 14, wherein:
the mobile transponder includes a device identification, wherein the mobile transponder is further operable to transmit the device identification upon generating power from the radio frequency signal;
the sensor device includes:
a sensor circuit operable to generate the measurement value;
a scanning antenna operable to generate the radio frequency signal; and
a transceiver operable to receive the device identification;
wherein the message including the measurement data is transmitted only after the device identification is received.

17. The patient data gathering system of claim 14, wherein the sensor device includes:
a scanning antenna operable to generate the radio frequency signal; and a transceiver operable to transmit the measurement data; and wherein the scanning antenna and the transceiver are switched from a sleep mode to a wake mode when the measurement value exceeds a threshold value, and wherein the sleep mode uses less power than the wake mode.

18. The patient data gathering system of claim 14, wherein the sensor device is selected from a group consisting of: a weight sensor device including a weight sensor circuit, a pulse/oxygen sensor device including a pulse and oxygen sensor circuit, a blood pressure sensor device including a blood pressure sensor circuit, a temperature sensor device including a temperature sensor circuit, a blood glucose sensor device including a blood glucose sensor circuit, and an exercise device.

19. A method for delivering care for diabetes patients, the method comprising:
providing a diabetes kit to a patient, the diabetes kit including:
a blood glucose measurement device, wherein the blood glucose measurement device is operable to:
measure a blood glucose level of an individual;
generate a radio frequency field, wherein the radio frequency field has enough energy to power a mobile transponder associated with the individual; and
transmit a message including the measurement value; and a transponder associated with the individual, wherein the transponder includes a memory, and wherein the transponder is operable to:
generate power from the radio frequency field;
receive the message; and
store a data set to the memory, wherein the data set is derived from the message; and
download the data set from the transponder; and
use the data set as part of a medical service visit.

20. The patient data gathering system of claim 2, wherein the physical characteristic of the individual is a first characteristic of the individual, and wherein the mobile transponder further includes a measurement circuit operable to measure a second physical characteristic of the individual.

21. The patient data gathering system of claim 3, wherein the measurement circuit of the mobile transponder includes at least one circuit selected from a group consisting of: a blood pressure monitor circuit operable to detect a blood pressure of the individual, a weight sensor circuit operable to detect a weight of the individual, a pulse/oxygen sensor circuit operable to detect at least one of a pulse and an oxygen level of the individual, a temperature sensor circuit operable to detect a temperature of the individual, a blood glucose sensor circuit operable to detect a blood glucose level of the individual, and an exercise device circuit operable to detect one or more of an exercise time, an exercise distance, and an exercise calorie value.

* * * * *